United States Patent [19]

Pratt, Jr.

[11] 4,115,280

[45] Sep. 19, 1978

[54] APPARATUS FOR ALTERING THE BIOLOGICAL AND CHEMICAL ACTIVITY OF MOLECULAR SPECIES

[75] Inventor: George W. Pratt, Jr., Wayland, Mass.

[73] Assignee: Massachusetts Institute of Technology, Cambridge, Mass.

[21] Appl. No.: 601,122

[22] Filed: Jul. 31, 1975

Related U.S. Application Data

[62] Division of Ser. No. 88,528, Nov. 12, 1970, Pat. No. 3,941,670.

[51] Int. Cl.$^2$ .............................................. B01K 1/00
[52] U.S. Cl. .................................................. 250/527
[58] Field of Search .............. 204/DIG. 11; 250/527; 21/54 A, 102 A, DIG. 2

[56] References Cited

U.S. PATENT DOCUMENTS

| | | | |
|---|---|---|---|
| 3,227,642 | 1/1966 | Lemelson | 250/527 |
| 3,443,087 | 5/1969 | Robieux et al. | 204/DIG. 11 |
| 3,458,140 | 7/1969 | Schryver | 204/DIG. 11 |
| 3,539,221 | 11/1970 | Gladstone et al. | 241/1 |
| 3,657,085 | 4/1972 | Hoffmeister | 204/DIG. 11 |
| 3,672,823 | 6/1972 | Boucher | 21/102 A |
| 3,699,210 | 10/1972 | Binning et al. | 204/DIG. 11 |
| 3,710,279 | 1/1973 | Ashkin | 204/DIG. 11 |
| 3,719,454 | 3/1973 | Shang | 23/252 R |

FOREIGN PATENT DOCUMENTS

| | | | |
|---|---|---|---|
| 690,681 | 7/1964 | Canada | 204/DIG. 11 |
| 671,922 | 5/1952 | United Kingdom | 21/54 A |

OTHER PUBLICATIONS

Cool et al., Applied Physics Letters, vol. 15, No. 10, (15 Nov. 69) pp. 318 and 319.

Electronics, Nov. 24, 1961, pp. 54–57.
Osial, Instruments & Control Systems, Oct., 1967, pp 101–104.

Primary Examiner—Howard S. Williams
Attorney, Agent, or Firm—Arthur A. Smith, Jr.; Rober Shaw

[57] ABSTRACT

Apparatus for altering (i.e., deactivating or activating the biological or chemical activity of macromolecula species that employs laser beam radiation at a frequenc$\gamma$ that excites vibrational and rotational states of the irra diated species and at an intensity sufficient to activat( the species (but below the denaturation level) or to ; level such that the weak bonds — e.g., hydrogen bond — that determine the spatial character, and hence th( biological activity of macromolecules are irreversibl$\gamma$ broken to such extent that the macromolecule loses it original form (the process of denaturation) and assume an inactive (denatured) configuration. In the case o absorbing materials, pulses of energy from the beam which are obtained by interrupting a c.w. beam, using pulsed laser, or as a Q-switched configuration, are used In a broad sense, the invention is primarily directed t( the breakdown of large molecules either into varietie with different spatial characteristics or into smalle molecular units. This is effected by exposure to lase radiation which excites vibrational and rotational state of the irradiated species to such an extent that substan tially irreversible chemical changes take place. Thes changes can in some instances occur in the species itsel without the presence of any other reacting chemic$\epsilon$ agents. In other instances, the laser may effect a chang by enhancing or retarding a chemical reaction amon different species.

56 Claims, 17 Drawing Figures

APPARATUS FOR ALTERING THE BIOLOGICAL AND CHEMICAL ACTIVITY OF MOLECULAR SPECIES

This is a division of application Ser. No. 88,528, filed Nov. 12, 1970 (now U. S. Pat. No. 3,941,670) and is being filed to comply with a requirement for restriction.

The present invention relates to methods of and means for altering the activity the macromolecular species by exposing said species to laser radiation in a particular frequency range to excite rotational and vibrational levels in the species at a particular intensity level and for a sufficient period of time to produce either reversible or irreversible changes therein; these changes can in some instances occur in the species itself without the presence of any other chemical agent as, for example, in the process of inactivation, or in other cases the radiation may enhance or retard a chemical reaction by activating one or more participants.

It has been known that electromagnetic radiation can alter the chemical and/or biological properties of many substances. Thus, for example, sterilization by gamma rays, $\beta$-rays, x-rays and ultra violet light have been extensively investigated. The discovery underlying the present invention is that infrared radiation in a relatively narrow band of frequencies (e.g., 3 to 30 microns) introduced into the vibrational and/or rotational states of certain complex organic molecules has an unusually large influence upon the irradiated molecules. The process hereinafter described employs high energy infrared laser radiation sources which, by way of illustration, can be a $CO_2$ laser which can produce c.w. radiation levels in the kilowatt range and pulses in the megawatt power range. Furthermore, it is now possible to tune the frequency of high power infrared lasers over a considerable range (5 microns to 20 microns). These high powers over a range of frequencies allow the efficient transfer of large amounts of energy into macromolecular organic systems. It has been found for present purposes that this energy transfer can be due to absorption of the laser radiation into electronic levels of the molecules, but, also, and more importantly, into the excitation of vibrational and rotational levels. Furthermore, the high power densitites available allow the absorption of significant amounts of power.

The Raman spectra of many amino acids, nucleic acids, and biopolymers that are the molecular structures of greatest interest herein, have vibrational and rotational absorptions in a range from 350 $cm^{-1}$ to 3500 $cm^{-1}$, more or less. There is a nonlinear coupling of a vibrating molecular bond to an electromagnetic ambient field of appropriate frequency. In order that the field induce amplitudes of vibration or rotation so large that molecular bonds will be either reversibly or irreversibly broken, an intense radiation source is necessary and preferably one that can be tuned to obtain any resonant enhancement possible. Lasers operating in the above frequency range, e.g., $CO_2$ lasers which operate at 10.6 microns and CO lasers which operate in a range from 5.2 to 6 microns, are ideal radiation sources. Not only are they capable of delivering enormous pulse powers, e.g., in the megawatt range, and very large c.w. powers, e.g., in the kilowatt range, but they can also be tuned, for example, using frequency doubling techniques and spin-flip Raman scattering.

Tunable Raman scattering may be accomplished in at least two ways. First, it is possible to tune continuous stimulated spin-flip Raman scattering, e.g., in InSb as reported by Mooradian et al. (Appl. Phys. Lett,1970). Secondly, it is possible to vary the elastic constants of the Raman scatterer by altering its carrier concentration which in turn alters the elastic constants of the scatterer and hence its vibrational frequencies, as hereinafter discussed.

It should be further noted that the biological activity of many macromolecular species or biopolymers depends upon rather weak bonds as discussed in Chapter IV of J. D. Watson's book "Molecular Biology of the Gene." These bonds can be effectively broken by exposure of the macromolecule to laser radiation either by direct absorption of the energy or indirectly. The indirect process starts with the absorption of electromagnetic radiation by vibrational and/or rotational modes involving covalently bound atoms. For example the skeletal frequencies lying in the 800 to 1150 $cm^{-1}$ range for Ribonuclease or the "breathing" mode of the monosubstituted phenyl ring at 1006 $cm^{-1}$ in phenyl alanine would be strongly excited by a $CO_2$ laser operating at 10.6 or 9.6 microns. Large amplitude oscillations of this type can lead to the destruction of weaker bonds and cause the molecule to lose its original form, i.e., become denatured or deactivated by assuming an inactive configuration. This is to be contrasted with burning wherein the process of combustion occurs.

The invention disclosed herein is described in greatest detail in connection with sterilization whereby macromolecular configurations are deactivated by laser radiation. It is to be noted, however, that some aspects of the present teaching make it useful in connection with processes wherein such macromolecules are activated. The sterilization process has been found to be particularly useful in connection with the deactivation of dry Bacillus subtilis spores. In tests conducted in connection with the present invention, a spore sample of approximately $10^7$ spores distributed over 3 $cm^2$ on acetate paper was exposed to an unfocused $CO_2$ laser beam of 23 watts power for 1/10 of a second. All the spores struck by the beam were rendered completely inactive. That is to be compared with required exposure times 600 to 10,000 times longer in steam at 170° C. to obtain the same effect. In similar tests, exposure of a paper substrate to the same laser beam for 1/25 of a second did not burn or otherwise substantially damage the paper.

Infrared radiation is almost totally reflected from metallic surfaces. Consequently, a metallic or other highly reflecting object can be exposed to an intense laser beam for prolonged periods of time, seconds or hundreds of seconds depending on the laser power, without the transfer of damaging amounts of energy to the reflecting material. Electromagnetic waves incident upon a metallic surface combine with reflected waves to produce a vanishing tangential electric field for an ideal metal. For normal incidence the tangential component of the electric field reaches a maximum at odd multiples of 80/4, where $\lambda$ is a wavelength of the radiation. For a $CO_2$ laser $\lambda = 10.6$ microns. Consequently, macromolecular species of size considerable less than $\lambda/4$ in extent from the metal surface would lie on a space of low electric field and would be unable effectively to couple to and absorb energy from the laser beam. Consequently, oblique incidence of the laser beam to the metal surface is used. It can be shown that the electromagnetic field is then described as a combination of a standing and travelling wave. Wherever the tangential component of the E field vanishes, the normal component reaches a maximum, and, when the normal component vanishes, the tangential component is a maximum.

Infrared laser radiation incident obliquely on a metallic or other highly reflecting surface provides an excellent means for rendering that surface sterile, which is useful in sterilizing surgical instruments, metallic vessels and tanks, metallic pipes, needles, etc. This radiation process is accomplished by sweeping the beam over the surface of these objects by moving the laser, using moving mirrors, or moving the object itself or any combination of these means, as later discussed. A further important use for the present teaching is the sterilization of highly reflective packaging material such as aluminum foil. The foil is passed under the beam in such a way that the entire area required to be sterile is exposed to the beam. In order that the laser beam intercept as large an area as practical for a given position of the surface and laser, the laser beam can be reflected obliquely back and forth between the foil surface and a reflecting surface as hereinafter discussed.

Accordingly, a principal object or the present invention is to provide a new and useful method of sterlization, one which employs laser radiation of particular frequencies, intensities, and time durations.

The energy required to deactivate surface contaminants is small compared to that required to significantly damage an absorbing material. Therefore, the invention can be used to sterilize plastics, cloth, glass, as well as foodstuffs that are subject to spoilage or other deterioration due to surface contamination. A particularly useful technique when dealing with such absorbing material is the use of high energy, short time duration laser pulses achieved by operation of the laser in a pulsed or Q-switched configuration. Still another object of the invention, therefore, is to provide laser apparatus adapted to irradiate macromolecular species disposed on surfaces of materials which are attacked by the laser radiation, but to maintain the level of intensity or time of exposure, or a combination thereof below magnitudes sufficient to cause undesirable damage to the absorbing surface.

A further object is to provide laser apparatus adapted to irradiate macromolecular species and in particular those responsible for infection such as viruses, bacteria, and the like, as well as bacteria and enzymes which may be disposed on reflecting or absorbing surfaces, in partially transparent liquids or in gases; this aspect of the invention has particular application in medical situations in operating rooms and the like wherein a sterile atmosphere is highly desirable such as burn recovery and certain types of surgical procedures, in the process of pasteurization, and for the purpose of controlling a process such as fermentation.

A still further object is to provide laser apparatus adapted to sterilize flesh laid bare in a medical procedure where surface contamination of the bare tissue is to be prevented; in this instance the laser is pulsed so that only a monomolecular layer of tissue and the contaminants thereon are biologically deactivated.

The foregoing objects may be classified loosely as being directed to a method of activating (i.e., changing the level of activity thereof) or deactivating (i.e., inactivating) biological type macromolecules. The invention has use, however, in connection with other molecular species as well. Thus, by way of illustration, it can be used to perform catalytic action in an oil cracking operating wherein complex molecules are broken down into less complex molecules. Broadly, therefore, the objects of the invention are to teach a method of irradiation of a macromolecular or complex molecule species wherein laser radiation is introduced into the vibrational and/or rotational states of the species thereby to affect the activity of the irradiated molecules.

Yet another aspect of the invention is that of activating molecules to change, for example, the rates at which spores, viruses and the like multiply or to change the rate at which less complex molecules enter into chemical reactions; this is accomplished, again, by introducing laser radiation at a frequency which excites the vibrational and rotational states of the irradiated species, but in this instance the intensity of such radiation is kept below a level which would deactivate spores, viruses and living molecules and below a level which would change the form of the less complex molecules.

Since, as above mentioned, particular frequencies of laser radiation or a particular band of frequencies may best serve the purposes herein discussed, it is necessary to provide such frequencies or sweep the band of frequencies to function as intended. A still further object is, therefore, the provide in laser apparatus, means for choosing a particular frequency output and for shifting or sweeping that output as well as to provide means for detecting the effect of such radiation as a function of frequency, intensity, etc.

These and still further objects will be evident upon reference to the descriptive portion of the specification hereinafter and are particularly delineated in the appended claims.

By way of summary, the objects are embraced by a process for altering (e.i., deactivating and activating) the biological activity of macromolecular species (e.g., living cells, enzymes, spores, viruses, bacteria and other cells and combinations of cells) and the chemical activity of further molecular species (e.g., high molecular weight hydrocarbons), the process, in the latter case, acting, in effect, like a catalyst. The species are subjected to laser radiation at a frequency that excites the vibrational and rotational states thereof; for example, in the case of spores, etc. a frequency of interest is the 10.6 micron output of the $CO_2$ laser. The intensity of radiation is maintained at a level high enough to effect such altering, but the level of such intensity and the time of exposure are kept to less than some combination which would affect adversely the material upon which the species rest or at an appropriate level to provide desired catalytic action. The intensity level and time duration aspect is of consequence in pasteurization or sterilization uses of the process wherein the species is located on plastic, paper and the like which ae destructible by laser frequencies and intensities of the range most useful in the sterilization or pasteurization process herein described; or when the species is in a fluid containing one or more constituents which are destructible by laser frequencies and intensities of the range most useful in the sterilization or pasteurization process herein described.

The invention is described hereinafter upon reference to the accompanying drawings in which:

FIG. 9b is a modification of the apparatus of FIG. 9a;

Figure 1:
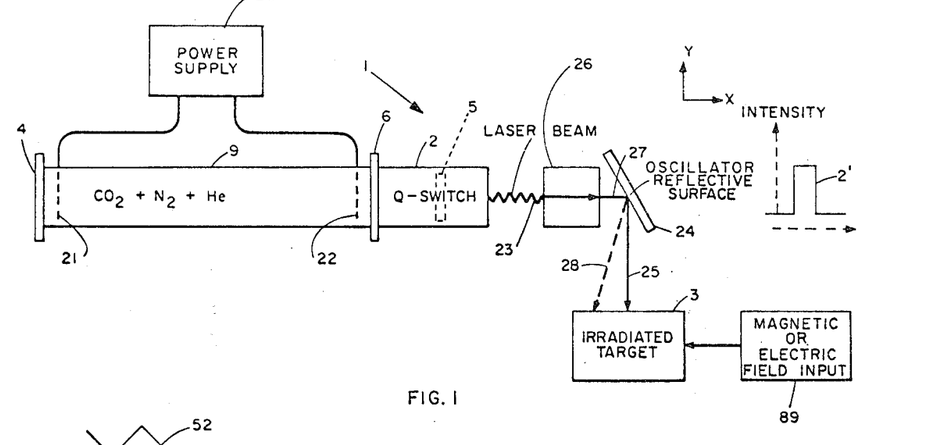
FIG. 1 is a diagrammatic representation of an embodiment of the present invention and shows, schematically, a laser apparatus adapted to irradiate a target with Q-switched radiation which may be passed into a frequency selecting or tuning device whose output is directed onto the target.

Turning now to FIG. 1, apparatus is shown generally at 1 for altering (deactivating or activating) the biological and/or chemical activity of macromolecular species which may be located in the block labeled 3 and described as an irradiated target. Such altering, as discussed above, is effected by irradiating the macromolecular species by directing thereupon radiation from a $CO_2$ laser 9 (that contains $CO_2$ as well as $N_2$ and He gases) which produces, by the process of stimulated emission, radiation primarily at 960.99 $cm^{-1}$ and 1063-77 $cm^{-1}$. The laser 9 may be Q-switched as shown at 2 to provide short, intense bursts of radiation. The emitted radiation numbered 23 may further be frequency shifted, modulated, or tuned by a device 26. The radiation is directed upon the target 3 by a mirror arrangement 24 which may be capable of oscillatory motion for the purpose of sweeping the beam over the target. Work done to date has been primarily with dry *Bacillus subtilus* spores, as later discussed herein, which are made up at least in part of macromolecular species or biopolymers which control the biological activity of said spores. The deactivation of said spores is an important aspect of the present invention. Radiation from the laser 9 excites vibrational and rotational states of the irradiated spores located at the target 3, the large amplitudes of induced oscillation in the spores being sufficient to disrupt these macromolecules to the extent that they are no longer biologically active. This disruption and disorientation is physical or mechanical and is not of the nature of the chemical reaction that obtains in a burning process. Said another way, the spores are inactivated but not necessarily (or desirably) burned. This inactivation can be effected by correlating the time of exposure and beam intensity, by the use, for example, of a shutter or a chopper to pass and not pass the beam, or by the use of the Q-switch 2 which produces a very high intensity, but very short pulse 2'. The Q-switch embodies a rotatable mirror 5 forming a cavity which emits radiation at one angular position only thereof and is capable of quite large intensity build-up between pulses. The frequency shifter, selector, or modulator at 26 is used to pick out radiation whose frequency is particularly adapted to inactivate or activate the target. The optical cavity in the embodiment of FIG. 1 is between the mirror 5 and a mirror 4. The mirror 4 can be a grating which can also be used as a frequency selector by varying the angle at which radiation strikes the grating.

Figure 6:
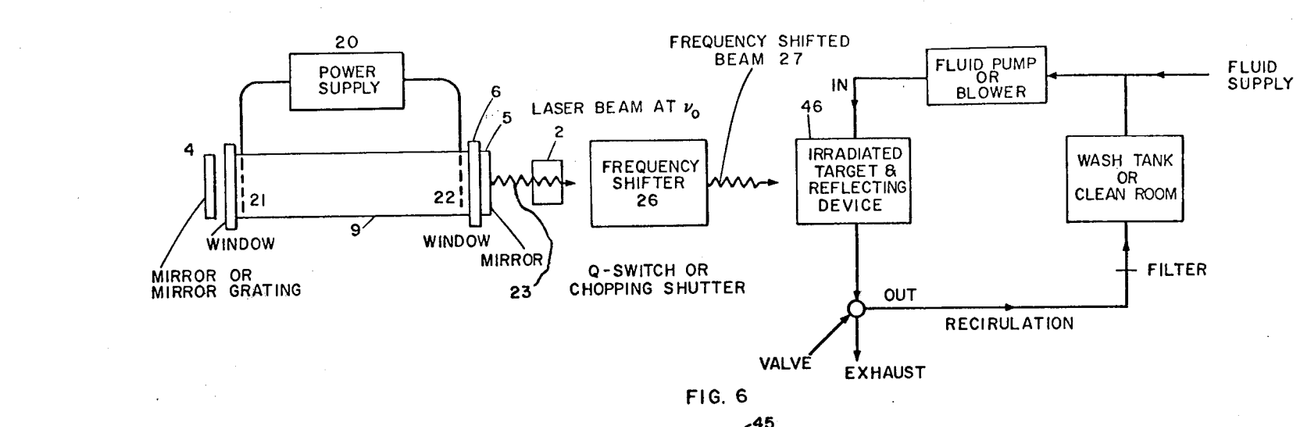
FIG. 6 is an embodiment similar to FIG. 1 in which the beam may be or may not be Q-switched or pulsed and the particular frequency may be selected by using the left-hand mirror or mirror-grating combination and/or frequency shifts might be produced by a Raman scattering cell to provide the beam which finally impinges upon a target.
Figure 11:
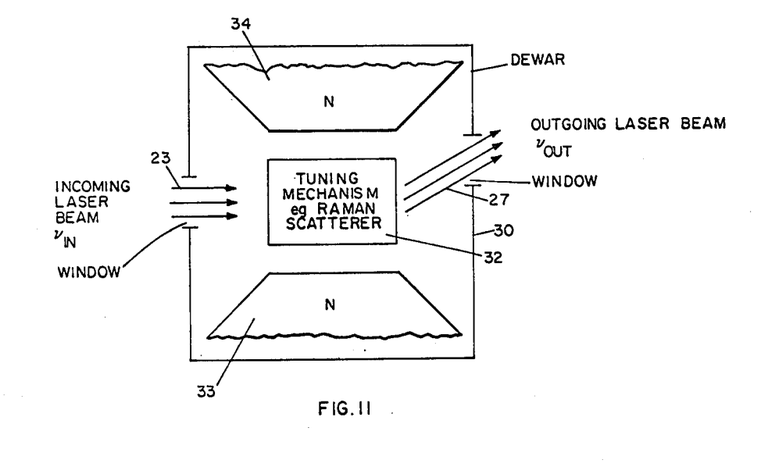
FIG. 11 shows, schematically, an arrangement for altering the frequency of a laser beam to select a particular frequency using a Raman scattering cell, the Raman scattering being tuned by using a magnetic field to alter spin flip Raman scattering frequencies or by varying the elastic constants of the scatterer.
Figure 12:
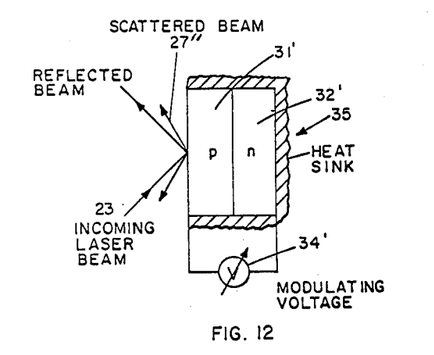
FIG. 12 shows, schematically, apparatus used to frequency shift and frequency modulate an incoming laser beam by varying the elastic constants of a semiconductor forming part of a diode whose bias is supplied by a modulated voltage source, the modulated signal appearing in the scattered beam.
Figure 13:
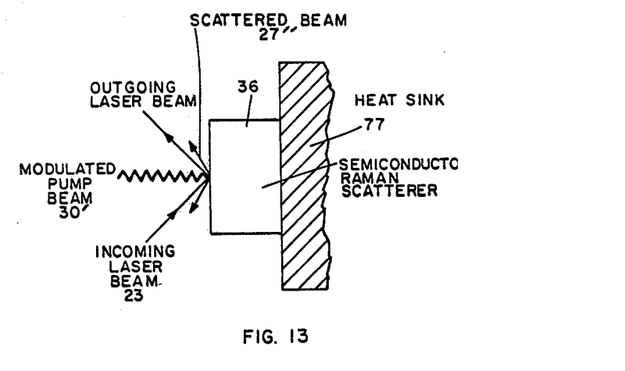
FIG. 13 shows, schematically, apparatus used to frequency shift and frequency modulate an incoming laser beam by varying the elastic constants of a semiconductor wherein the incident beam is directed to an area also illuminated by an amplitude modulated pump beam which alters the electron-hole concentrations in the region where it is absorbed, the amplitude modulated pump signal being converted into a frequency modulated scattered laser beam.

The optical cavity defined by the mirror or mirror-grating 4 and the mirror 5 which, as mentioned, may include a Q-switch, contains a gaseous medium adapted to receive energy from electrodes 21 and 22 energized by a d-c power supply 20 to produce, in the enclosed space within the gaseous laser medium between the mirror or mirror-grating combination 4 and a window 6, an inverted population of energy states so that electromagnetic radiation therein is amplified by the process of stimulated emission. The reflecting surface 5 is partially transparent to allow the laser beam 23 to emit from the optical cavity. The beam 23 in FIG. 1 and in FIG. 6 is shown entering a frequency shifting device 26 which may be used to select a frequency particularly adapted to be effective upon the target to-be-irradiated, although frequency shifting is not always necessary. The frequency shifted beam labeled 27 in FIG. 1, is shown reflected by the oscillatory reflective surface 24 to cover a portion of the target between the position shown at 25 and 28, respectively, thereby to spread over a larger area the characteristically smaller laser beam. This oscillation is shown to be in the $x$-$y$ plane but it can go into the $y$-$z$ plane, as well. The target may be moved, as well, to effect a greater coverage by the laser beam. The laser 1, as mentioned, lases at 10.6 microns, primarily. However, other frequencies may be selected by use of a grating-mirror combination 4 in which the angle of the grating is varied to provide effective optical feedback to the cavity at frequencies which vary with the position of the grating. Further control of the frequency may be achieved by the frequency shifting, or modulating, or tuning device 26 which may be one of several mechanisms. One such means for shifting the frequency is to employ at 26 spin flip Raman scattering of the entering laser beam 23, as shown in FIG. 11, by an InSb crystal 32 suitably cooled by liquid nitrogen and placed in a variable magnetic field (represented by pole pieces 33 and 34) whose strength determines (the order of 10,000 gauss), at least in part, the frequency of the Raman scattered beam. (The Raman scatterer 32 can also be ferroelectric such as $BatiO_3$, $LiNbO_3$, and the elements 33 and 34 can be plates electrically charged to provide a field the order of kilovolts/cm.) Another means of shifting the frequency is to use Raman scattering wherein the elastic constants of the Raman scatterer are changed or modulated as shown in FIGS. 12 and 13. In FIG. 12 the elastic constants of the p-side of a diode 35 are varied by varying the voltage output of a potential source 34' applied between the p-side numbered 31' and n-side numbered 32'. The scattered beam labeled 27" is frequency modulated as a consequence of modulating the elastic constants of the crystal 35. The device can be arranged so that the beam 23 strikes the n-side 32' instead of the p-side 31'. In FIG. 13, the elastic constants of a semiconductor scatterer 36 are varied by subjecting the scatterer 36 to a modulated pump beam 30' which alters the number of electrons and holes in the scatterer 36 which is temperature controlled by a heat sink 77. The pump beam 30' is arranged to strike the scatterer at the same spot struck by the incident beam 23. The variation of elastic constants with carrier concentration is detailed in a work of R. W. Keyes, I.B.M. Journal 5, 266 (1961). By the foregoing methods the frequency of the beam can be swept so as to in react effectively with the vibrational and/or rotational levels of the target materials. The frequency modulation methods discussed above are also useful in the transmission of information in communications.

Figure 2:
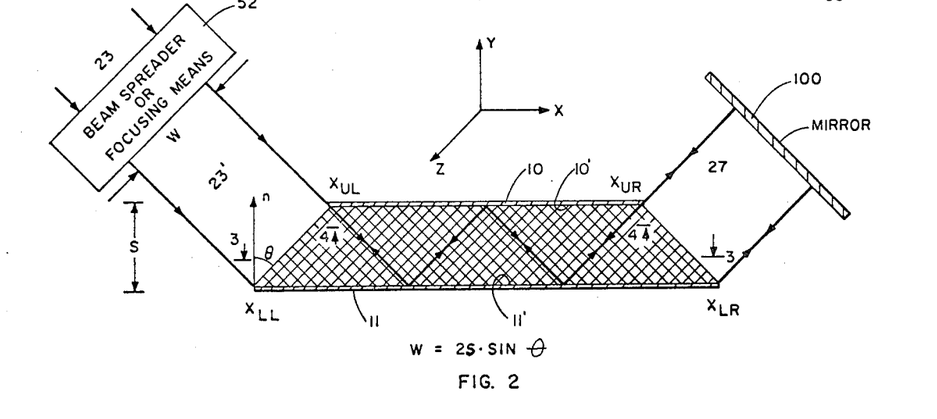
FIG. 2 shows, diagrammatically, an arrangement whereby the characteristically small laser beam, which may arise from the laser of FIG. 1, is reflected between the surfaces of reflecting plates or other media so as to fill the entire volume between the plates defined by the cross-hatched area in the x-y plane and of thickness $t$ in the $z$ direction, $t$ being the thickness in the $z$ direction of the incoming laser beam, whose width in the x-y plane is W as shown.
Figure 3:
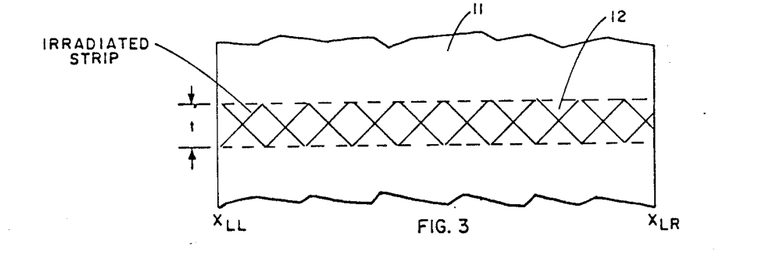
FIG. 3 is a view taken upon the line 3—3 in FIG. 2 looking in the direction of the arrows.
Figure 4:
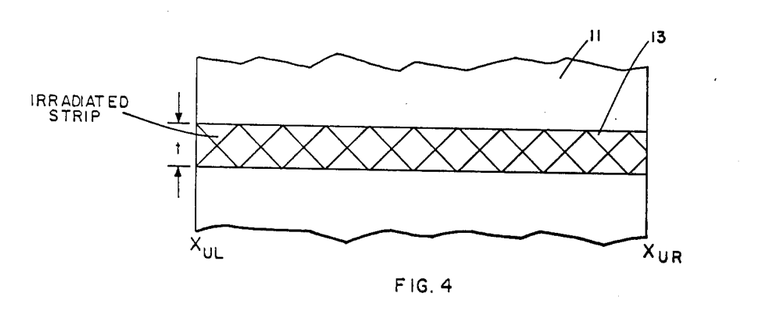
FIG. 4 is a view taken upon the line 4—4 in FIG. 2 looking in the direction of the arrows.
Figure 5:
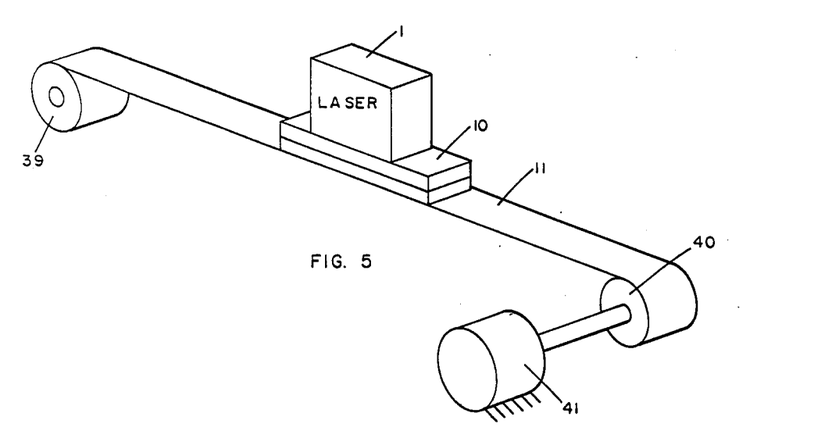
FIG. 5 shows, schematically, an arrangement for effecting longitudinal movement of the target material of FIG. 1 which appears as a strip, foil, or ribbon in FIG. 5, transverse motion between the beam and strip material being accomplished, for example, by a pivoting mirror scheme as indicated in FIG. 1.

In FIG. 2 the laser radiation 23 is shown entering a beam expander or focussing means 52 the output beam 23' from which is directed upon the reflecting surface 11' of a moving sheet or metal strip 11 in order to sterilize that reflecting surface. (The sheet 11 can contain a thin liquid film upon the surface 11', as later mentioned, to provide exposure of the film and any macromolecules carried therein to selective radiation frequencies thereby to affect the carried molecules.) The radiation in the illustrative example has cross dimensions W and is directed at an angle $\theta$ to the normal $n$ to the planar surface of the strip 11. A sheet 10 having lower surface 10' is shown disposed in a closely-spaced plane parallel to the plane of the surface 11'. The beam is directed at the surface 11' at an angle $\theta$ no greater than $\sin^{-1} W/2S$, where S is the distance between the upper surface of 11' of the strip 11 and the lower surface 10' of the sheet 10. In actual apparatus, the reflecting strip or ribbon 11 may be moving sheet of aluminum foil or other material which it is desired to sterilize on the upper surface thereof as the foil moves from a roll 39 to a roll 40, as shown in FIG. 5, the roll 40 being driven by an electric drive designated 41. The laser beam is shown reflecting back into the space between the upper surface 10' and the lower surface 11' by a mirror 100; the reflected beam can be caused to pass back across the surfaces to irradiate other strips similar to the strips designated 12 and 13 in FIGS. 3 and 4. In FIG. 2 the ribbon 11 moves longitudinally (i.e. the $z$ direction) into or out of the paper and the beam is reflected to move transversely (i.e., the $x$ direction) of the moving sheet 11.

Figure 7:
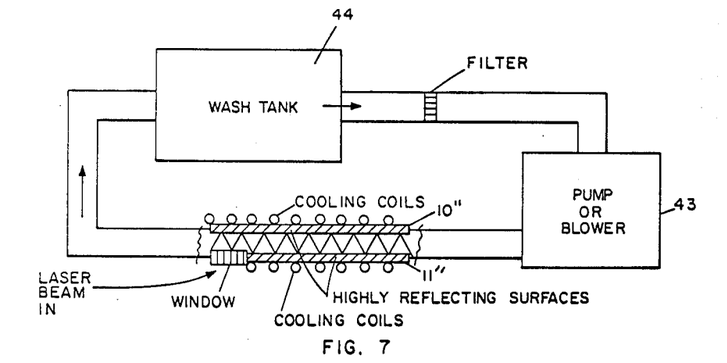
FIG. 7 is a diagrammatic representation of apparatus wherein a liquid is used to wash an object and the liquid which is partially transparent to the beam is thereafter sterilized by a laser beam, the representation being intended to illustrate, as well, apparatus adapted to pass air or some other gas past the laser beam.
Figure 8:
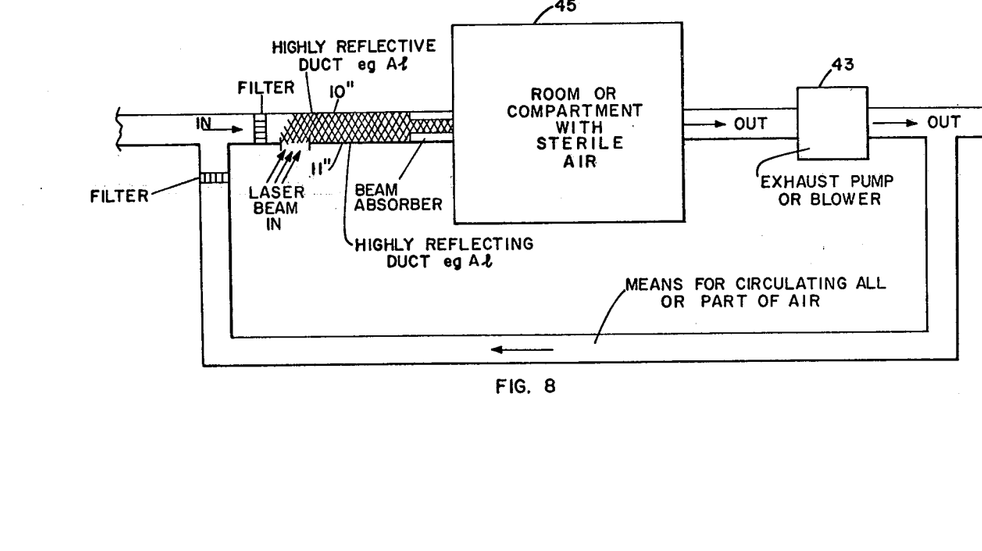
FIG. 8 is a further diagrammatic representation of apparatus wherein the air entering a room is sterilized by passing through a duct filled with radiation.

Of course, neither the upper nor the lower surface need move and the gap therebetween can contain a gas, such as air, or a liquid which can be sterilized as it passes between the reflective surfaces; and the arrangement shown diagrammatically in FIGS. 7 and 8 can be used. In these figures a pump 43 moves a fluid, gas or partially absorbant liquid, into the region between the reflecting surfaces of an upper plate 10" and a lower plate 11". The fluid can be a liquid used in connection with a washing operation in a wash tank 44 in FIG. 7; or the element 43 can be a blower and the fluid can be a gas recirculated from an operating room 45 in a hospital for sterilization by the laser beam of the room air, as shown in FIG. 8. The sterilization of the air or other fluid as it passes between the plates 10" and 11" is accomplished because of the rapid biological inactivation possible using laser beams of appropriate frequencies, as discovered by the present inventor and as discussed herein. The process is particularly useful in sterilizing air because spores and the like carried by air are physically separated from one another and the inactivation thereof can be effected in milliseconds or less; however, spores and the like located on material surfaces have some thickness and the outer layers tend to absorb the laser radiation and to protect the lower layers; also, spores and the like in water or some other solutions are somewhat protected by solution absorption of the radiant energy. Thus, higher beam intensities may be necessary adequately to expose multi-layer spores, or selective frequencies may be needed to inactivate spores in solution. The process is also useful in controlling the activity of enzymes in a process such as fermentation.

In the apparatus of FIG. 6, much of the apparatus shown is duplicative of FIG. 1 or other figures and to that extent the same number designations are applied; other elements are merely named since, again, they are discussed elsewhere herein. The illustrative example shown does disclose, schematically, a more complete apparatus than in some of the other figures and does differ somewhat in other particulars. For example, a mirror 5' is shown at the right side of the optical cavity for use in instances in which the Q-switch 2 is replaced by a chopper or other device.

As discussed elsewhere herein, irradiation of a metal or other reflecting surface has the definite advantage of the reinforced electric field effect of the laser radiation near the surface. Also, a metal surface can be irradiated for a substantial time period to insure complete inactivation of the spores and the like in those instances in which there is some substantial thickness of the material to be inactivated. However, the principal value of the present discovery is the capability of the appropriate-frequency radiation of relatively modest intensity to inactivate or denature in a very, very short time period. This makes possible the sterilization of air and some other fluids, (e.g. Nujol, carbon disulphide ($CS_2$) and benzene ($C_6H_6$)) but it makes possible, as well, the sterilization of plastics and other substances that cannot be sterilized of such things as B. subtilus short of destruction of the substance, as by burning, since prior art practice requires exposure of the B. subtilus to 170° C. temperature of the order of 3 hours. Thus, the present discovery allows faster sterilization, but it permits, as well, sterilization that was not heretofore possible (for example, paper is not suitable for heating in an autoclave under steam, however, sterilization of a paper surface is possible here). One more point is of interest. Mention has been made that the deactivation or denaturing process does not, or at least need not, involve burning or combustion of the spores, viruses, bacteria or cells denatured. For that reason, the deactivation time is quite short, and the amount of energy absorbed in the deactivation process is quite small. The inventor has found that life, even in the hard-to-deactivate spores and the like, can be terminated relatively easily by attacking the organism at its weakness.

In the foregoing discussion, the combination of exposure time and beam intensity is emphasized, and one way of controlling the magnitude of both is mentioned in connection with Q-switching. It should be evident from the discussion also that the laser beam can be c.w. and that the exposure time of macromolecules on the surface 11' in FIGS. 2-5 will be a function of the moving velocity of the strip 11; and, similarly, the exposure time of macromolecules in the embodiments of FIGS. 7 and 8 will depend upon the velocity of movement of the fluid between the plates 10" and 11". And in either situation the exposure time, of course, can be increased by reflecting the beam back and forth to create a plurality of strips 12, for example. Also, the intensity can be varied by a beam expander or focusing means 52 which can act upon the incoming beam 23 and provide the input beam 23' to the surface 11'. Tests have shown that even thin paper or cellulose samples such as thin filter material can be exposed to radiation of the order of 23 watts/cm$^2$ for 1/25 second without destroying the filter, and in tests conducted dry B. subtilus spores were inactivated as above discussed. The exposure time that a material will withstand depends, of course, on the mass of the material undergoing radiation as well as the material itself. Certainly, cellulose filters represent a class of easily damaged materials. The effect of the input radiation upon the backing material or the fluid within which the species is carried or the exposed species itself is determined also by the frequency of the input radiation, and recent developments have made very precise (the order of one hundred cycles or less) frequency control. Also, there is selective enhancement by non-linear coupling of a vibrating molecule of the species to the electromagnetic field of the input radiation as mentioned elsewhere herein.

Figure 10:
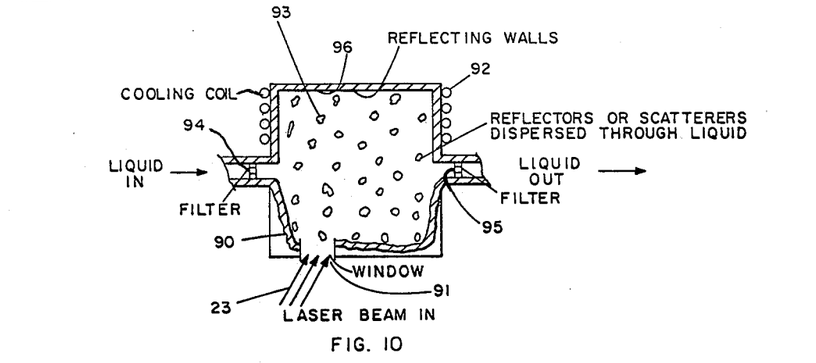
FIG. 10 shows an arrangement for scattering an incoming laser beam throughout a reflection cell (partially cutaway) by using reflecting bodies within the liquid in the cell, which are contained therein by the filters at the input and output ports of the cell.
Figure 16:
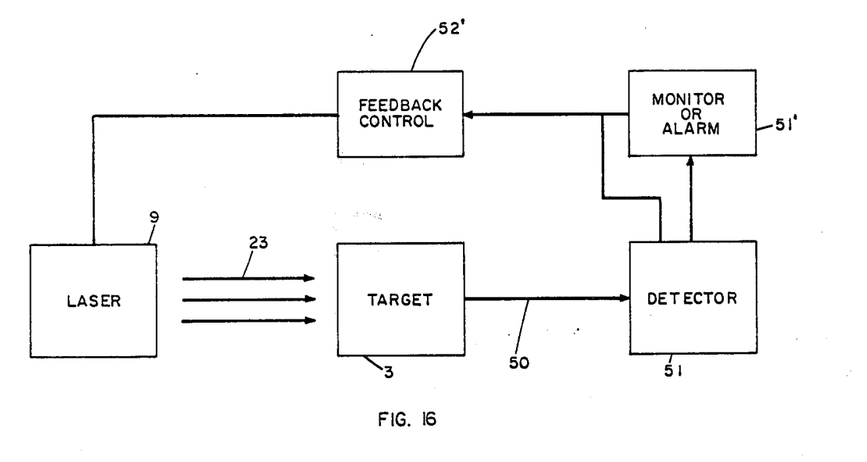
FIG. 16 shows in block diagram form, an arrangement whereby laser radiation directed upon a target area is reflected, transmitted or scattered and detected, and the detected radiation functions as an output or as a control signal.

The apparatus of FIG. 10 can be used in a system similar to that shown in FIG. 7 to replace the reflecting plates 10" and 11". In FIG. 10 the laser beam 23 is introduced to a cell or housing 90 through a window 91 as before, to pass into and through the liquid contained in said housing and be reflected by reflective walls 96. The radiation within the cell 90 is also scattered by reflectors 93 which are suspended in the liquid and kept in the cell by a pair of filters 94 and 95. In this way, the whole of the liquid within the cell volume receives the full intensity of the laser beam. A cooling coil 92 serves to remove laser introduced heat energy from the liquid. The embodiment of FIG. 10 is of particular use in a pasteurization process as, for example, in the production of alcoholic beverages. Again, the laser can be a $CO_2$ laser adapted to radiate principally at 10.6 and 9.6 microns; or a CO laser adapted to radiate at many frequencies between 5 and 6.2 microns; or a YAG: Nd$^{+3}$ solid-state laser adapted to radiate at about 1 micron. Also the output radiation frequency from the particular laser used can be modulated and filtered to produce substantially one determined frequency and the amplitude can also be controlled, thereby selectively to affect particular macromolecular species (of many disposed within the liquid in the cell 90) while having a lesser effect on others; in addition, frequencies can be found to which the liquid is transparent. Furthermore, a detector as discussed in connection with FIG. 16 can be used to measure or determine the effect of the radiation on said particular species. Some aspects of the invention discussed in this paragraph have applicability in connection with the other embodiments discussed elsewhere herein.

Figure 9A:
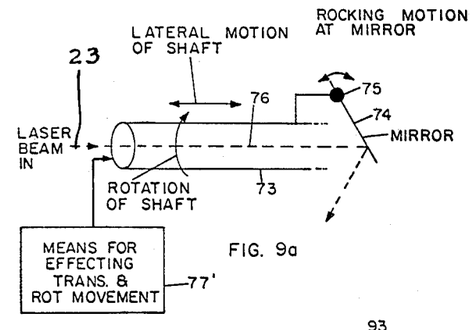
FIG. 9a is a diagrammatic representation of apparatus used to disperse and spread the beam over the walls of a surface which surrounds the device shown and said device may be moved into and out of a volume surrounded by the walls to-be-sterilized.
Figure 9B:
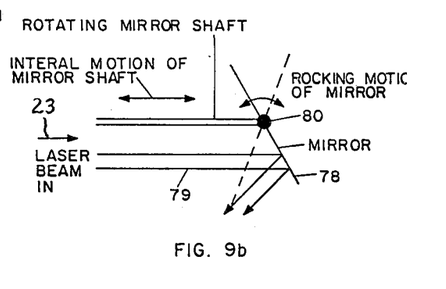
Figure 14:
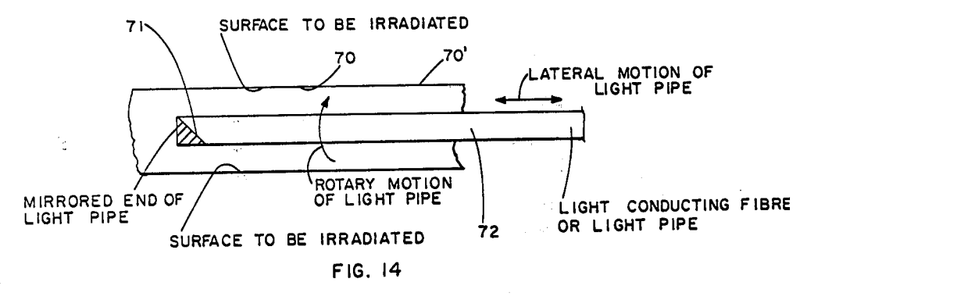
FIG. 14 is a diagrammatic representation of a light conducting fibre or pipe used to convey sterilizing radiation to the interior walls of a tubular surface, the entire wall area being swept by the light beam by rotating the light pipe whose end is mirrored at an angle so as to divert the reflected light to the walls, the light pipe being allowed to move in a lateral fashion into and out of the tubular cavity.
Figure 15:
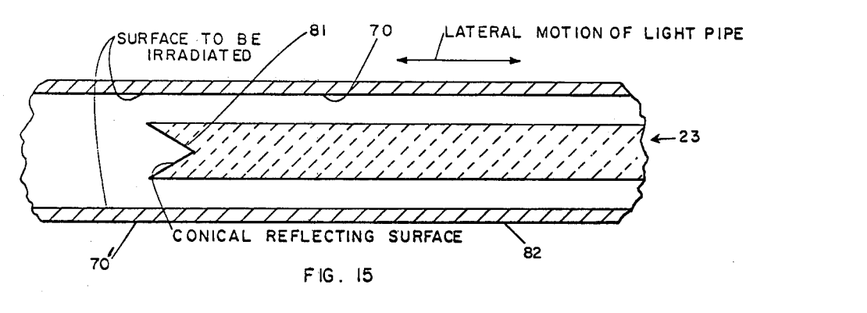
FIG. 15 is a diagrammatic representation, partially cutaway, similar to the representation in FIG. 14 except that the light beam is reflected by a conical surface.

The discussion in this paragraph relates to apparatus adapted to irradiate the inner surfaces of a cavity (large or small) which may be a cylinder, container, vessel or even a region within the human body, the purpose of such irradiation being, broadly, to affect biological activity in the region of such irradiation. One such apparatus is shown in FIG. 9a, wherein the laser radiation 23 is shown directed into a light pipe 73 to be reflected by a mirror 74 pivotally attached at 75 to the light pipe. As is indicated in the figure, the light pipe 73 can be moved laterally along its axis 76 or rotationally about its axis. Means for effecting lateral and rotational movement of the pipe 73 is shown in block diagram form at 77'. In FIG. 9b, a mirror 78 is shown pivotally attached at 80 to a hollow shaft 79 adapted to vibrate to the left and right in FIG. 9b and to rotate. The light pipe can be the light conducting fibre shown at 72 in FIG. 14 and having a mirrored end surface 71 inclined to the fibre axis to reflect incoming light to the interior surface 70 of a cylinder 70'. Again, the pipe is capable of axial and/or rotational movement. A similar light pipe or fibre is shown at 82 in FIG. 15. The light pipe or fibre 82 has an inwardly axially oriented conical reflecting surface 8 at its terminating end adapted to spread the incoming beam 23 to the inner surface of the cylinder 70', as before.

The deactivation process discussed in greatest detail herein is concerned with very large molecules such as the double helix type discussed in the Watson reference, spores, etc. Such macromolecules contain hydrogen bonds which are the bonds generally disrupted by the input radiation (but are not necessarily the bonds which couple to the input radiations); this hydrogen bond is dipole and is one which couples quite readily with radiation of appropriate frequency. The deactivating process is one wherein a relatively small amount of laser irradiation acts to disrupt the bond and the actual deactivation is effected then by the normal thermal type agitation which is always present in these species but which is, normally, not of destructive proportions. Said another way, the laser radiation acts to disrupt the binding forces of the molecules and allows the molecules to be torn asunder by the other forces which act within these complex molecules. Thus, a relatively small packet of laser radiation can perform the deactivation function. This is to be contrasted with burning wherein energy is introduced primarily to the electronic levels of the molecules and in which the resulting action is chemical, requiring the presence of other chemicals.

Another aspect of the invention is that of activating molecules to change, for example, the rates at which spores, viruses and the like multiply or to change the rate at which enzymes and less complex molecules enter into chemical reactions. This is accomplished, again, by introducing laser radiation at a frequency which excites the vibrational and rotational states of the irradiated species, but in this instance the intensity of such radiation is kept below a level which would change the form of the molecules. The activating process may be likened to that of a catalyst in chemical processes whereby a chemical reaction can be made to occur with greater facility. By way of further illustration, the activating process is useful in the petroleum cracking industry wherein complex molecules are broken down into less complex molecular structures.

The thermal agitation before discussed can be replaced by other forces such as high magnetic background fields (i.e., 12,000 gauss and up) and high field gradients (the order of 1300 kilogauss per centimeter) to provide a dividing or other force; and such field can be high a electric background field as well. Both fields are represented by the block shown at 89 in FIG. 1. Or the species acted upon can be subjected to a high stress in the form of a pressure or shock wave to provide and enhance the dividing force. Such shock wave can be produced by well-known mechanical means. Also, the laser beam itself can create pressure or shock waves in gaseous, liquid and solid media. Such shock waves can best be provided by Q-switching or pulsing the laser to provide very short exposure of the gas, liquid or solid to very high intensity laser radiation. In this way, the laser provides the irradiating means as well as the shock generating or creating means. The medium can be in a substantial volume, as the fluids shown in FIGS. 7 and 8, or it can be in the form of a thin layer of film such as might be located on the surface 11' in FIG. 2; and in any of the gas, liquid or solid mediums, the shock wave can even detonate an explosion. It is to be appreciated that the disruptive or dividing forces discussed in this paragraph have some or probably greatest use in connection with chemical acts, such as the cracking process before mentioned, rather than the strictly biological aspects, but the biological aspects are of some importance.

In FIG. 16 incident radiation 23 from the laser 9 is delivered or directed upon the target 3 and the scattered or transmitted radiation from the target, labeled 50 in the figure is picked up by a detector 51. In this way, the nature of the macromolecular species in the target area and the effect thereon of the laser radiation is determined by measuring the scattered or transmitted or reflected radiation 50 as a function of frequency amplitude, and time. The detector 51 can be connected to a feedback control 52 to modify appropriately the output of the laser 9. The detector 51 can be gold-doped germanium or copper-doped germanium or a pyroelectric detector. Also, the detector 51 could activate an alarm 51' or other like device in the event of failure of the laser or other vital elements of the system, and this type arrangement can be included in the circuitry of FIGS. 5,6,7 and 8. Also, the biological or chemical activity of different macromolecular species can be altered selectively by varying the frequency and/or amplitude of the laser beam, and and this too can be monitored.

A number of terms are used herein to denote similar actions, but the terms are not necessarily identical. The term "alter" is used to define a situation wherein molecules are activated or a situation wherein molecules are deactivated. The term "deactivate" is used to embrace "denaturation" as well as "inactivation" although the former is more properly concerned with protein cells and the latter is more properly concerned with bacteria generally. The term "activate" is intended to embrace, among other things, a catalytic effect which may, be way of illustration, accelerate or make possible a chemical reaction such as the cracking of petroleum before discussed.

Further modifications of the invention will occur to persons skilled in the art.

What is claimed is:

1. Apparatus for altering by irradiation the biological activity of macromolecular species on a surface which moves relative to the incident radiation, that comprises, in combination, means for generating laser radiation, means for frequency selection, tuning, and/or modulation of the radiation to produce radiation which directly excites vibrational and rotational and, potentially, electronic states of the irradiated species, said radiation being in the infrared region of the electromagnetic spectrum, means for directing the beam of laser radiation upon the surface, means for effecting relative movement between the surface and the irradiating beam in any combination of longitudinal and transverse directions so that each part of the surface that is irradiated by the beam is irradiated for only a fraction of a second, and means for spreading the characteristically small cross-dimensional laser beam to enlarge the portion of the surface irradiated as the surface passes across the beam.

2. Apparatus as claimed in claim 1 in which the means for spreading the laser beam comprises: two reflective surfaces disposed in closely-spaced parallel planes, one of the two surfaces being a moving surface, the beam being directed at an angle of incidence ($\theta$) to one of the two surfaces, where $\theta$ is the angle between the incoming beam and a normal drawn between the two planes and is no greater than sin−1W/2S, where W is the width of the incoming beam and S is the distance separating the two plates.

3. Apparatus as claimed in claim 2 which includes means to expand the beam before it is directed into the space between the parallel reflecting plates.

4. Apparatus as claimed in claim 1 in which the irradiating beam is focused so as to increase the incident power density.

5. Apparatus as claimed in claim 1 in which said radiation lies in the range between 350 $cm^{-1}$ and 3500 $cm^{-1}$.

6. Apparatus for altering the biological activity of macromolecular species on a moving surface by irradiation, that comprises, means for generating laser radiation as a laser beam at a frequency which excites vibrational and/or rotational states of the irradiated species and for directing the beam upon the surface, means for effecting relative movement between the surface and the laser in the longitudinal direction to receive radiation from the laser beam to expose at least part of said surface to laser radiation for only a fraction of a second, and means for spreading the characteristically small cross-dimension laser beam to irradiate the surface in the lateral direction as the surface passes in front of the beam, said frequency being in the infrared region of the electromagnetic spectrum.

7. In sterilization apparatus adapted to destroy living cells, spores and other like macromolecular species, a laser adapted to introduce to the species laser radiation at a frequency that is characteristic of the binding force between various constituents of the species thereby to introduce a disruptive effect to said binding force and to allow other disruptive forces that affect such species to cause the species to divide and thereby be destroyed, said frequency being in the infrared region of the electromagnetic spectrum.

8. Apparatus as claimed in claim 7 that includes means for controlling the frequency, amplitude and time to exposure of the macromolecular species to said laser radiation, thereby selectively to deactivate one or more macromolecular species of a group of said species.

9. Sterilization apparatus as claimed in claim 8 in which the species are disposed upon a backing material which can be destroyed by said radiation and in which the time of exposure is long enough to destroy the cells but not long enough to destroy the backing material.

10. Sterilization apparatus as claimed in claim 8 which displays a Q-switch laser pulse.

11. Apparatus as claimed in claim 8 in which the level of laser radiation to which the cells are subjected is at least 23 watts/cm$^2$ and the time of exposure is the order of 1/10 second or less.

12. Apparatus as claimed in claim 11 in which the laser is a $CO_2$ laser, adapted to radiate at about 10.6 and 9.6 microns.

13. Apparatus as claimed in claim 8 in which the means for controlling is an adjustably timed opening through which the laser radiation must pass before reaching said macromolecular species.

14. Apparatus as claimed in claim 7 in which the laser is a CO laser adapted to radiate between 5 and 6.2 microns.

15. Apparatus as claimed in claim 7 in which the laser is a YAG: $Nd^{+3}$ solid state laser adapted to radiate at about 1 micron.

16. In apparatus adapted to alter chemical and/or biological activity of macromolecular species by irradiation, a laser adapted to introduce to the species laser radiation that contains an envelope of frequencies, at least one of the frequencies in said envelope of frequencies being one that excites vibrational and rotational states of the irradiated species, the range of said frequencies being in the infrared region of the electromagnetic spectrum.

17. In apparatus as claimed in claim 16, means for modulating the laser radiation to change the frequencies included in the envelope of frequencies, thereby to sweep through a substantially broad band of frequencies to expose the species to a relatively large number of radiative frequencies in the course of such exposure.

18. Apparatus as claimed in claim 16 in which the laser beam is pulsed to provide very short exposure o the species to a very high intensity laser radiation.

19. Apparatus for altering the biological or the chemical activity of molecular species contained within a gas liquid or solid medium by irradiation, that comprises means for generating laser radiation as a laser beam at a frequency and intensity which excites vibrational and /or rotational states of the medium and thereby create a shock wave in the medium, and means for effecting relative movement between the beam and the medium said frequency being in the infrared region of the electromagnetic spectrum.

20. Apparatus as claimed in claim 19 in which the laser beam is Q-switched to provide very short exposure of the gas, liquid or solid medium to very high intensity laser radiation.

21. Apparatus as claimed in claim 19 in which the laser beam is pulsed to provide very short repeated exposure of the gas, liquid or solid to very high intensity laser radiation.

22. Apparatus for altering the biological or the chemical activity of macromolecular species on the interior surface of a cavity by irradiation, that comprises, means for generating laser radiation as a laser beam at a frequency which excites vibrational and/or rotational states of the irradiated species, said frequency being in the infrared region of the electromagnetic spectrum, means for directing the beam upon the surface, means for sweeping the beam over the interior surface area and means for controlling the frequency, amplitude and time duration of the radiation.

23. Apparatus as claimed in claim 22 in which the means for directing beam upon the interior surface o the cavity and for sweeping the radiation over the interior surface of the cavity comprises a reflecting surface upon which the entering radiation is directed and thence reflected upon the surface to be irradiated, th reflecting surface being capable of being rotated abou an axis parallel to the entering beam and capable o lateral motion parallel to that axis.

24. Apparatus as claimed in claim 22 that include means for detecting failure in the apparatus and in which the means for detecting failure comprises power meter upon which is directed a portion of th entering beam, and output of said power meter bein fed to a monitoring device.

25. Apparatus as claimed in claim 22 in which th means for directing beam upon the surface and mean for sweeping same over the surface comprises a ligh pipe terminated by a reflecting surface so disposed tha the radiation emerging from the light pipe falls upon portion of the surface to be irradiated, the light pip being capable of at least one of rotary motion about i axis and lateral motion along its axis.

26. Apparatus as claimed in claim 25 in which th light pipe is a light conducting fibre having a conic reflecting surface.

27. Apparatus as claimed in claim 22 which includ means controlling the beam width of said radiation.

28. Apparatus as claimed in claim 27 in which mea is provided for spreading said beam.

29. Apparatus for altering by irradiation the biolog cal and/or chemical activity of macromolecular speci which are a constituent of a liquid that moves relative the incident radiation, that comprises, means for gene ating laser radiation, means for frequency selectio tuning, and/or modulation of the radiation to produ radiation which excites vibrational and rotational and potentially electronic states of the irradiated species, the frequency of the radiation being in the infrared region of the electromagnetic spectrum, means for effecting movement of the liquid through the irradiating beam to expose each part of the liquid to the laser radiation for only a fraction of a second, means for spreading the characteristically small cross-sectional laser beam to irradiate a complete volume element as the liquid flows under the beam.

30. Apparatus as claimed in claim 29 in which means for spreading the laser beam comprises a container with highly reflecting walls through which the liquid is circulated and which contains additional reflecting bodies dispersed through the liquid.

31. Apparatus as claimed in claim 30 in which the means for effecting movement of liquid comprises means for passing the liquid under the beam in the form of a film.

32. Apparatus for altering by irradiation the biological and/or chemical activity of molecular species, that comprises, in combination, means for generating laser radiation and for directing said radiation upon said species, means for frequency selection, tuning, and/or modulation of the radiation to produce radiation which excites vibrational and rotational states of the irradiated species, the frequency of the radiation being in the infrared region of the electromagnetic spectrum, means for adjusting the frequencies and intensity of said laser radiation to effect nonlinear coupling of said radiation to the vibrational and rotational states of the irradiated species, and means for effecting relative movement between the laser radiation and the irradiated species to provide exposure of the species to the laser radiation for only a very short time period.

33. Apparatus as claimed in claim 32 that further includes means for subjecting the irradiated species to a high magnetic field gradient substantially at the same time as irradiation occurs.

34. Apparatus as claimed in claim 32 that further includes means for subjecting the irradiated species to a high electric field substantially at the same time as irradiation occurs.

35. Apparatus as claimed in claim 32 that further includes means dividing the species substantially at the same time as irradiation occurs.

36. Apparatus as claimed in claim 35 wherein the means dividing comprises means for applying a pressure or shock wave to the species.

37. Apparatus as claimed in claim 32 wherein said species is disposed upon a catalytic surface and wherein the beam is directed upon the species on the surface, whereby a chemical reaction is accelerated or made possible by virtue of a catalytic effect.

38. Apparatus as claimed in claim 32 wherein said species is disposed upon a surface and wherein the beam is directed upon the species on the surface, whereby a chemical reaction is accelerated or made possible.

39. Apparatus adapted to catalytically break down complex molecular species into less complex molecular species that comprises, in combination:
chamber means to receive said complex molecular species;
means for introducing the complex molecular species to the chamber;
means for introducing laser radiation to the chamber means at a frequency which selectively excites vibrational and rotational states of at least one of the irradiated species, said frequency being in the infrared region of the electromagnetic spectrum, the selective excitation acting to provide a disruptive or dividing force in connection with the chemical act of catalytic breakdown of said complex species; and
means for removing the less complex molecular species from the chamber.

40. Apparatus as claimed in claim 39 having a material upon which the molecular species rest, which material provides a desired catalytic action; said apparatus having means to control at least one of the intensity and time duration of the laser radiation so that the material upon which the reacting species rests is not adversely affected and the desired catalytic action is provided.

41. Apparatus adapted to enhance catalytic action on molecular species that comprises, in combination: chamber means to receive said molecular species; means for introducing the molecular species to the chamber; catalytic means within the chamber adapted to effect catalytic action upon the molecular species therein; and means for introducing laser radiation to the chamber means at a frequency which selectively excites vibrational and rotational states of at least one of the irradiated species or of said catalytic means, said frequency being in the infrared region of the electromagnetic spectrum, the selective excitation acting to enhance the chemical act of catalytic action on said species.

42. Apparatus for separating a molecular species into its molecular constituents, that comprises, in combination, means for subjecting the molecular species to laser radiation at a frequency that is characteristic of the binding forces between some of the constituents of the molecules that form the molecular species and for directing the radiation upon the molecular species, said laser radiation acting to introduce a disruptive effect to said binding forces, said frequency being in the infrared region of the electromagnetic spectrum; means for controlling the frequency of the laser radiation and at least one of the intensity and time duration thereof to influence in a determined fashion the level of said disruptive effect; and means for simultaneously applying a dividing force between the constituents to separate one from the other during the occurrence of said disruptive effect.

43. Apparatus as claimed in claim 42 that includes means for subjecting the molecular constituents to a magnetic field gradient to provide said dividing force.

44. Apparatus as claimed in claim 42 that includes means for subjecting the molecular constituents to an electric field to provide said dividing force.

45. Apparatus as claimed in claim 42 that includes means for subjecting the molecular constituents to a magnetic field gradient and to an electric field to provide said dividing force.

46. Apparatus as claimed in claim 42 having means to subject the molecular constituents to a high stress in the form of a pressure or shock wave to provide and enhance the dividing force.

47. Apparatus for separating distinct molecular species from one another, that comprises: means for subjecting the distinct molecular species to laser radiation at a frequency that is characteristic of the vibrational and/or rotational frequencies of at least one of the species, said laser radiation acting to introduce selective excitation to said one of the species, said frequency being in the infrared region of the electromagnetic spectrum;

means for controlling the frequency of the laser radiation and at least one of the intensity and time duration thereof to influence in a determined fashion the level of said selective excitation; and means for simultaneously applying a dividing force to the irradiated species to separate one from another during the occurrence of said selective excitation.

48. Apparatus as claimed in claim 47 that includes means for subjecting the molecular species to a magnetic field gradient to provide said dividing force.

49. Apparatus as claimed in claim 47 that includes means for subjecting the molecular species to an electric field to provide said dividing force.

50. Apparatus as claimed in claim 47 that includes means for subjecting the molecular species to a magnetic field gradient and to an electric field to provide said dividing force.

51. Apparatus as claimed in claim 47 having means to subject the molecular species to a high stress in the form of a pressure or shock wave to provide and enhance the dividing force.

52. Apparatus for altering the chemical characteristics of a molecular species to affect the rate at which the molecules of said molecular species enter into chemical reactions, that comprises, in combination: means generating laser radiation at a frequency that excites at least one of the vibrational states and the rotational states of the irradiated species and directing the laser radiation upon the molecular species to effect a change of state of said molecules of said molecular species and, hence, the chemical characteristics thereof, said frequency being in the infrared region of the electromagnetic spectrum, said means generating laser radiation being adapted to generate such radiation at a frequency which effects nonlinear coupling of the radiation to said at least one of the vibrational states and the rotational states of said molecules; and means effecting a chemical reaction of the thusly excited molecular species.

53. Apparatus as claimed in claim 52 wherein said radiation lies in the range between 350 cm$^{-1}$ and 3500 cm$^{-1}$.

54. Apparatus for separating distinct molecular species from one another, the molecular species being disposd in a medium that includes a plurality of said distinct molecular species, that comprises, in combination: means subjecting the plurality of distinct molecular species in the medium to laser radiation at a frequency which selectively excites at least one of the vibrational state and the rotational state of one of the irradiated species and as a consequence of the selective excitation changes the state of said one irradiated species and hence its chemical character, the change of state of said one of the irradiated species being effected solely by the irradiation at said frequency, said frequency being in the infrared region of the electromagnetic spectrum, said means subjecting being adapted to generate such radiation at a frequency which effects nonlinear coupling of the radiation to said at least one of the vibrational state and the rotational state of molecular species; and means for simultaneously effecting a chemical reaction of the molecular species of said plurality to cause a selective chemical reaction thereof.

55. Apparatus as claimed in claim 54 wherein the change of state of each molecule of the irradiated species is effected by absorption of a single photon.

56. Apparatus as claimed in claim 54 wherein said laser radiation lies in the range between 350 cm$^{-1}$ and 3500 cm$^{-1}$.

* * * * *